United States Patent
Mello et al.

(10) Patent No.: US 9,271,565 B2
(45) Date of Patent: Mar. 1, 2016

(54) MOUTHWASH FORMULATIONS FOR USE WITH TOOTHBRUSH DELIVERY DEVICE

(75) Inventors: Sarita Mello, North Brunswick, NJ (US); Madhusudan Patel, Somerset, NJ (US); Sharon Kennedy, Randallstown, MD (US); Thomas Boyd, Metuchen, NJ (US); Evangelia S. Arvanitidou, Princeton, NJ (US); James R. Brown, Edison, NJ (US); Suman Chopra, Monroe, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 311 days.

(21) Appl. No.: 13/812,423

(22) PCT Filed: Jul. 30, 2010

(86) PCT No.: PCT/US2010/043825
§ 371 (c)(1),
(2), (4) Date: Feb. 12, 2013

(87) PCT Pub. No.: WO2012/015420
PCT Pub. Date: Feb. 2, 2012

(65) Prior Publication Data
US 2013/0330116 A1   Dec. 12, 2013

(51) Int. Cl.
| A45D 24/00 | (2006.01) |
| A45D 7/00 | (2006.01) |
| A46B 11/00 | (2006.01) |
| A61K 8/34 | (2006.01) |
| A61K 8/49 | (2006.01) |
| A61Q 11/00 | (2006.01) |

(52) U.S. Cl.
CPC .............. *A46B 11/00* (2013.01); *A46B 11/001* (2013.01); *A61K 8/34* (2013.01); *A61K 8/4926* (2013.01); *A61Q 11/00* (2013.01); *A46B 2200/1066* (2013.01); *A61K 2800/244* (2013.01); *A61K 2800/87* (2013.01)

(58) Field of Classification Search
CPC ....... A61Q 11/00; A61K 8/4926; A61K 8/34; A61K 2800/244; A61K 2800/87; A46B 11/001; A46B 11/00; A46B 2200/1066
USPC ............. 132/311, 200, 308, 320; 424/49–58; 514/900, 901, 902; 15/167.1, 21.1; 401/136–139
See application file for complete search history.

(56) References Cited

U.S. PATENT DOCUMENTS

| 3,356,095 A * | 12/1967 | Tylle ............................ 132/311 |
| 3,734,106 A * | 5/1973 | Zimmerman ................ 132/311 |
| 3,864,472 A * | 2/1975 | Pensak et al. ................... 424/54 |
| 3,947,570 A * | 3/1976 | Pensak et al. ................... 424/54 |
| 4,060,870 A | 12/1977 | Cannarella |
| 4,067,962 A * | 1/1978 | Juneja .............................. 424/52 |
| 4,224,307 A * | 9/1980 | Thiele et al. ..................... 424/49 |
| 4,325,939 A * | 4/1982 | Shah ................................ 424/55 |
| 4,476,107 A * | 10/1984 | Schmolka ........................ 424/49 |
| 4,569,837 A * | 2/1986 | Suzuki et al. .............. 514/772.2 |
| 4,716,035 A | 12/1987 | Sampathkumar |
| 4,923,685 A * | 5/1990 | Wuelknitz et al. .............. 424/54 |
| 4,990,329 A | 2/1991 | Sampathkumar |
| 5,100,650 A * | 3/1992 | Carlin et al. .................... 424/52 |
| 5,102,251 A | 4/1992 | Kaufmann |
| 5,309,590 A * | 5/1994 | Giuliani et al. ................ 15/22.1 |
| 5,330,748 A * | 7/1994 | Winston et al. ................. 424/49 |
| 5,352,052 A | 10/1994 | Kaufmann |
| 5,405,604 A | 4/1995 | Hall |
| 5,407,287 A | 4/1995 | Braun et al. |
| 5,661,170 A * | 8/1997 | Chodosh ........................ 514/390 |
| 5,686,063 A * | 11/1997 | McLaughlin et al. .......... 424/54 |
| 5,723,106 A * | 3/1998 | Buch et al. ...................... 424/49 |
| 5,769,553 A * | 6/1998 | Chaudhri et al. ............. 401/195 |
| 5,776,435 A | 7/1998 | Gaffar et al. |
| 5,829,976 A | 11/1998 | Green |
| 5,842,487 A * | 12/1998 | Ledet ............................ 132/308 |
| 5,948,390 A * | 9/1999 | Nelson et al. ................... 424/54 |
| 6,015,547 A * | 1/2000 | Yam ................................ 424/49 |
| 6,089,776 A | 7/2000 | Kaufmann |
| 6,095,707 A | 8/2000 | Kaufmann |
| 6,121,315 A * | 9/2000 | Nair et al. ...................... 514/494 |
| 6,164,858 A | 12/2000 | Kaufmann |
| 6,183,155 B1 | 2/2001 | Kaufmann |
| 6,205,611 B1 | 3/2001 | Vigil |
| 6,322,268 B1 | 11/2001 | Kaufmann et al. |
| 6,497,527 B2 | 12/2002 | Kaufmann |
| 6,607,711 B2 * | 8/2003 | Pedersen ......................... 424/49 |
| 6,669,390 B1 | 12/2003 | Porter et al. |
| 6,723,305 B2 * | 4/2004 | DePierro et al. ................ 424/54 |
| 6,902,337 B1 | 6/2005 | Kuo |
| 6,932,603 B2 | 8/2005 | Han et al. |
| 6,932,604 B2 | 8/2005 | Han et al. |
| 7,124,894 B1 | 10/2006 | Dobos |
| 7,311,456 B1 | 12/2007 | Neal |
| 7,401,373 B2 * | 7/2008 | Tybinkowski et al. ............ 15/29 |

(Continued)

FOREIGN PATENT DOCUMENTS

| DE | 3113450 | 10/1982 |
| EP | 0244363 | 11/1987 |

(Continued)

OTHER PUBLICATIONS

Anonymous, "Betaisodona-Mund-Antiseptikum," Mar. 1, 2002, Mar. 1, 2012, pp. 1-2; XP007918113.

(Continued)

Primary Examiner — Vanitha Elgart

(57) ABSTRACT

Disclosed are compositions suitable for use with an oral care implement. The compositions provide improved sensory appeal, and comparable reduction in volatile sulfur compounds and antibacterial activity to advanced formula toothpaste formulations. The compositions include a high percentage of antibacterial agent and flavoring, when compared to conventional toothpastes, and some mouth washes formulations, such that only minor amounts of the composition can be delivered to the oral care implement to provide improved reduction in volatile sulfur compounds, antibacterial efficacy, and optionally a cooling sensation.

10 Claims, No Drawings

(56) References Cited

U.S. PATENT DOCUMENTS

| | | | |
|---|---|---|---|
| 2001/0002228 A1 | 5/2001 | Owens | |
| 2003/0049327 A1 | 3/2003 | Zanone et al. | |
| 2003/0157206 A1 | 8/2003 | Paek | |
| 2003/0194678 A1 | 10/2003 | Viltro et al. | |
| 2005/0008584 A1* | 1/2005 | Montgomery | 424/53 |
| 2005/0026103 A1 | 2/2005 | Wasylucha | |
| 2006/0093558 A1* | 5/2006 | Lin et al. | 424/47 |
| 2007/0154863 A1 | 7/2007 | Cai et al. | |
| 2007/0254260 A1* | 11/2007 | Alden et al. | 433/85 |
| 2007/0292365 A1* | 12/2007 | Clarot et al. | 424/52 |
| 2008/0160056 A1* | 7/2008 | Boyd et al. | 424/401 |
| 2008/0176183 A1 | 7/2008 | Gatzemeyer et al. | |
| 2009/0053267 A1* | 2/2009 | DePierro et al. | 424/401 |
| 2009/0068122 A1* | 3/2009 | Pilch et al. | 424/52 |
| 2009/0074679 A1* | 3/2009 | Silverman | 424/53 |
| 2009/0317340 A1 | 12/2009 | Pak | |
| 2009/0317432 A1* | 12/2009 | Kergosien | 424/401 |

FOREIGN PATENT DOCUMENTS

| | | |
|---|---|---|
| EP | 0373758 | 6/1990 |
| EP | 0631771 | 1/1995 |
| EP | 1053744 | 11/2000 |
| EP | 1095660 | 5/2001 |
| EP | 1270580 | 1/2003 |
| EP | 2174649 | 4/2010 |
| FR | 2777459 | 10/1999 |
| JP | H10-236934 | 9/1998 |
| JP | 2006-506359 | 2/2006 |
| WO | WO 95/17159 | 6/1995 |
| WO | WO 01/62082 | 8/2001 |
| WO | WO 2005/009352 | 2/2005 |
| WO | WO 2007/011552 | 1/2007 |
| WO | WO 2008/091935 | 7/2008 |

OTHER PUBLICATIONS

Anonymous, "Salviathymol N," Jan. 1, 2008, pp. 1-2; XP007918045.

Ciobanu et al., "Antimicrobial mouthwash concentrate—inhibiting cariogenic buccal flora comprises alcoholic extract of plants, volatile oils and propolis tincture," WPI/Thomson, Mar. 25, 1992; XP002466823.

International Search Report & Written Opinion issued for corresponding International Application No. PCT/US2010/043825, mailed Apr. 28, 2011.

Dewhirst 1980, "Structure-Activity Relationships for Inhibition of Prostaglandin Cyclooxygenase by Phenolic Compounds," Prostaglandins 20(2):209-222.

\* cited by examiner

MOUTHWASH FORMULATIONS FOR USE WITH TOOTHBRUSH DELIVERY DEVICE

CROSS-REFERENCE TO RELATED APPLICATIONS

This application is a National Stage Entry under 35 U.S.C. §371 of International Patent Application No. PCT/US2010/043825, filed Jul. 30, 2010, (now expired), the contents of which is hereby incorporated by reference in its entirety.

BACKGROUND

Oral care implements, particularly toothbrushes, are typically used by applying toothpaste to a bristle section followed by brushing regions of the oral cavity, e.g., the teeth, tongue, and/or gums. Tooth brushing is part of a daily oral hygiene activity. Proper dental care involves regular flossing, brushing, rinsing with mouthwash and mouthrinses, and dental checkups. Dentists generally recommend that an individual brush his or her teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects. Dental checkups to a dentist office are typically the only feedback a person receives on their dental cleaning efforts. There is unfortunately plenty of time in between checkups for poor dental habits to cause problems. For example, gingivitis, periodontal disease, and a host of other problems can be magnified if dental cleaning habits are not rectified promptly.

Toothbrush devices with liquid collection systems are known in the art, including those having a capillary fluid system to wick the liquid from the collection area to the bristles. Such deviceds are disclosed and described in, for example, U.S. Pat. Nos. 5,102,251; 5,352,052; 5,769,553; 5,842,487; 6,089,776; 6,095,707; 6,164,858; 6,183,155; 6,322,268; 6,497,527; 6,669,390; 7,124,894; 7,311,456, as well as in U.S. Patent Application Publication Nos. 2007/0154863, 2008/0176183. Some toothbrushes have been equipped with fluid reservoirs and systems for delivering auxiliary active agents, such as whitening agents, breath freshening agents, and the like. The devices contain various transfer mechanisms that can transport the fluids to the brush or applicator (sponge, foams, etc.), including, for example, capillary channels constructed of wicking materials, vibration devices, squeeze triggers or pumps, and combinations of these.

Mouthwash and mouthrinse formulations also are well known in the art. Various formulations include antibacterial agents, flavorants, colorants, sweeteners, breath freshening agents, and the like. Appropriate dental hygiene typically includes brushing, flossing, and rinsing. It would be desirable to combine at least brushing with toothpaste, and rinsing with mouthwash into one procedure, making it easier to promote beneficial dental care. Thus, there exists a need to provide a device that provides adequate brushing and mouthrinsing capabilities, in which the formulation of the mouthwash or rinse is tailored to the device to provide sufficient quantities of active agents to the tooth surfaces.

SUMMARY

It is a feature of embodiments to provide compositions suitable for use with a brushing apparatus that provide improved sensory appeal, while at the same time provide comparable reduction in volatile sulfur compounds and antibacterial activity to advanced formula toothpaste formulations. It also is a feature of an embodiment to provide compositions having improved flavor profile, coupled with the ability to deliver malodor reduction and antibacterial activity with a minor amount of composition. It also is a feature of an embodiment to provide a composition that can be applied to the oral cavity in reduced quantities, but still deliver the same or greater amounts of active ingredient to the oral cavity, when compared to pastes and rinses. These and other features of embodiments may be achieved by providing a composition that includes a high percentage of antibacterial agent and flavoring, when compared to conventional toothpastes, and some mouth washes, such that only minor amounts of the composition can be delivered to the brushing apparatus to provide the results described herein.

In accordance with one embodiment, there is provided an oral care composition comprising 5 to 45% by weight antibacterial agent, 5 to 70% by weight flavorant, and an orally acceptable, liquid carrier, wherein the composition delivers more than 5 mg of antibacterial agent to the oral cavity when less than 50 μl of composition is delivered to the oral cavity, and wherein the composition has a viscosity of 1 to 100 mPas (cps).

In accordance with another embodiment, there is provided a system comprising a toothbrush having at least one applicator element and a transfer mechanisms for transferring an oral care composition from a reservoir positioned within the toothbrush to the surface of the at least one applicator element, and the oral care compositions described herein. The transfer mechanism for transferring may include wicking fibers, wicking foams, sponges, hydrogels, fluid passageways connecting a reservoir containing the composition to the filaments, vibration devices, pumps, and combinations thereof. The applicator element(s) may include bristles, foams, fibers, or other cleaning devices.

In accordance with another embodiment, there is provided a method of administering an antibacterial agent to the oral cavity of a mammal comprising applying the oral care composition to the oral cavity. The method also contemplates applying the composition to the oral cavity by using a toothbrush with at least one applicator element and a transfer mechanism for transferring the oral care composition from a reservoir positioned within the toothbrush to the surface of the at least one applicator element, wherein the composition is transferred from the surface of the at least one applicator element to the oral cavity.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, "antibacterial activity" herein means activity as determined by any generally accepted in vitro or in vivo antibacterial assay or test. "Anti-inflammatory activity" herein means activity as determined by any generally accepted in vitro or in vivo assay or test, for example an assay or test for inhibition of prostaglandin production or cyclooxygenase activity. "Antioxidant activity" herein means activity as determined by any generally accepted in vitro or in vivo antioxidant assay or test.

An "oral surface" herein encompasses any soft or hard surface within the mouth including surfaces of the tongue, hard and soft palate, buccal mucosa, gums and dental surfaces. A "dental surface" herein is a surface of a natural tooth or a hard surface of artificial dentition including a crown, cap, filling, bridge, denture, dental implant and the like. The term "inhibiting" herein with respect to a condition such as inflammation in an oral tissue encompasses prevention, suppression, reduction in extent or severity, or amelioration of the condition.

Classification herein of an ingredient as an active agent or a carrier ingredient is made for clarity and convenience, and no inference should be drawn that a particular ingredient necessarily functions in the composition in accordance with its classification herein. Furthermore, a particular ingredient can serve a plurality of functions, thus disclosure of an ingredient herein as exemplifying one functional class does not exclude the possibility that it can also exemplify another functional class.

Viscosity is measured at 25° C. using a Brookfield Viscosimeter employing a cone spindle at 10 rpm (2 degrees, 40 mm).

The oral care composition includes 5 to 45% by weight antibacterial agent, 5 to 60% by weight flavorant, and an orally acceptable, liquid carrier, wherein the composition delivers more than 5 mg of antibacterial agent to the oral cavity when less than 50 µl of composition is delivered to the oral cavity, and wherein the composition has a viscosity of 1 to 100 mPas (cps).

Suitable antibacterial agents include, without limitation, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435 to Gaffar et al. These antimicrobial agents are present in an antimicrobial effective total amount, typically 5% to 45%, for example 7% to 35%, 10% to 30%, or 15% to 25% by weight of the composition.

The antibacterial agent in certain embodiments is present in an amount such that the composition delivers more than 5 mg of antibacterial agent to the oral cavity when less than 50 µl of composition is delivered to the oral cavity. In certain embodiments, the composition delivers more than 5 mg of active agent, more than 6 mg, or about 7 mg or more of active agent, to the oral cavity when 45 µl of composition is delivered to the oral cavity.

In certain embodiments, the composition comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, a-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are present in a total amount of 5% to 70% by weight, 10% to 60% by weight, or 15% to 35% by weight, based on the total weight of the composition. In certain embodiments, the composition delivers more than 7.5 mg of flavorant to the oral cavity when less than 50 µl of composition is delivered to the oral cavity. In other embodiments, the amount delivered is more than 10 mg or more than 15 mg when less than 50 µl of composition is delivered to the oral cavity. In other embodiments the composition delivers more than 7.5 mg, 10 mg, or 15 mg when about 45 µl of composition is delivered to the oral cavity.

In certain embodiments, at least a portion of the flavorant includes a cooling agent. By "cooling agent" is to be understood any agent that imparts a cooling sensation to the skin and mucous membranes of the body, particularly the mouth, nose, throat and gastrointestinal tract during consumption. Cooling agents are known in the art, for example from US 7,090,832. The cooling agent used may be selected from the cooling agents listed above, such as menthol, menthol derivative compounds, menthyl acetate, menthyl lactate, acyclic and/or cyclic carboxamides, N-substituted paramenthane carboxamides, phosphine oxides, substituted p-menthanes, menthoxypropane, alpha-keto enamine derivatives, N- substituted p-menthane carboxamide, menthyl half acid ester derivatives, cubebol etc. In one embodiment, the cooling agent is a compound mixture comprising at least a menthol carboxamide compound. The cooling agent can be present in an amount of 5% to 70% by weight, 10% to 60% by weight, or 15% to 35% by weight, based on the total weight of the composition. In certain embodiments, the amount is 5 to 10% by weight. In certain embodiments, the composition delivers more than 2.5 mg of the cooling agent to the oral cavity when less than 50 µl of composition is delivered to the oral cavity. In other embodiments, the amount delivered is more than 3.5 mg or more than 5 mg when less than 50 µl of composition is delivered to the oral cavity. In other embodiments the composition delivers more than 2.5 mg, 3.5 mg, or 5 mg when about 45 µl of composition is delivered to the oral cavity.

The oral composition includes an orally acceptable carrier that is a liquid. In certain embodiments, water is selected as the orally acceptable, liquid carrier. In certain embodiments, the water is accompanied by an alcohol, e.g., ethanol. The weight ratio of water to alcohol can be generally 0.5:1 to 20:1, for example 0.75:1 to 10:1 or 1:1 to 7:1.

In certain embodiments, the composition optionally further comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, sucralose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.01% to 15% by weight of the composition, or 0.1% to 10% by weight.

In various embodiments, the compositions may be formulated with conventional dentifrice components, including, for example, at least one humectant, at least one abrasive material, and the like. In various embodiments, the oral care compositions do not include abrasive materials, although their use is optional.

The compositions described herein may be formulated with optional other ingredients, including without limitation anticaries agent, anticalculus or tartar control agents, anionic carboxylate polymers, viscosity modifiers, surfactants, flavorants, pigments, signals (flavor, color, light, heat, smell and other signals that signal the efficacious or advantageous use of the composition), essential oils, agents to treat dry mouth, and the like.

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N, N,N- tris(2-ethanol)-dihydrofluoride).

As anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride is the sole fluoride-releasing salt present, illustratively an amount of 0.01% to 5%, 0.05% to 1% or 0.1% to 0.5%, sodium fluoride by weight can be present in the composition. Other anticaries agents can be used, such as arginine and arginine derivatives (e.g., ethyl lauroyl arginine (ELAN)).

Phenolic compounds useful herein illustratively include, subject to determination of oral acceptability, those identified as having anti-inflammatory activity by Dewhirst (1980), Prostaglandins 20(2), 209-222, but are not limited thereto. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, thymol, and biphenols obtainable from extracts of the plant Magnolia officinalis. These phenolic compounds typically are present in one or more of the natural extracts described above.

The at least one phenolic compound is optionally present in a total amount of 0.5% to 30% by weight. Illustratively the total concentration of the at least one phenolic compound in a mouth rinse can be 1% to 20%, for example 3% to 15%, or 5% to 10%.

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez™ brand from ISP, Wayne, NJ. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically 0.01% to 50%, for example 0.05% to 25% or 0.1% to 15% by weight.

In various embodiments, the anticalculus system comprises a mixture of sodium tripolyphosphate (STPP) and a tetrasodium pyrophosphate (TSPP). In various embodiments, the ratio of TSPP to STPP ranges 1:2 to 1:4. In a one embodiment, the first anticalculus active ingredient, TSPP is present at 1 to 2.5% and the second anticalculus active ingredient, STPP is present at 1 to 10%.

In one embodiment, the anionic polycarboxylate polymer is present 0.1% to 5%. In another embodiment, the anionic polycarboxylate polymer is present 0.5% to 1.5%, or in one embodiment at 1% of the oral care composition. In one embodiment, the anticalculus system comprises a copolymer of maleic anhydride and methyl vinyl ether, such as for example, the Gantrez S-97 product discussed above.

In various embodiments, the ratio of TSPP to STPP to the synthetic anionic polycarboxylate ranges 5:10:1 to 5:20:10 (or 1:4:2). In one embodiment, the anticalculus system of the oral care composition comprises TSPP, STPP, and a polycarboxylate such as a copolymer of maleic anhydride and methyl vinyl ether at a ratio of about 1:7:1. In a non-limiting embodiment, the anticalculus system consists essentially of TSPP present at 0.5% to 2.5%, STPP present at 1% to 10%, and a copolymer of maleic anhydride and methyl vinyl ether present at 0.5% to 1.5%

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of 0.01% to 10%, for example 0.1% to 7% or 1% to 5% by weight of the composition.

In another embodiment the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc chloride, zinc gluconate, zinc glycinate, zinc oxide, zinc sulfate, sodium zinc citrate and the like. One or more zinc ion sources are optionally and illustratively present in a total amount of 0.05% to 3%, for example 0.1% to 1%, by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, α-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent other than the rosemary components described above. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

Compositions optionally contain other ingredients such as enzymes, vitamins and anti-adhesion agents. Enzymes such as proteases can be added for anti-stain and other effects. Non-limiting examples of vitamins include vitamin C, vitamin E, vitamin B5, and folic acid. In various embodiments, the vitamins have antioxidant properties. Anti-adhesion agents include ethyl lauroyl arginine (ELAN), ficin, silicone polymers and derivatives, and quorum sensing inhibitors.

Other optional materials that can be included are abrasives, bicarbonate salts, pH modifying agents, surfactants, foam modulators, thickening agents, viscosity modifiers, humectants, and colorants.

In a still further embodiment, the composition comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

If desired, the oral care composition described herein may include a surfactant, useful for example to compatibilize other components of the composition and thereby provide enhanced stability, to help in cleaning the dental surface through detergency, and to provide foam upon agitation, e.g., during brushing with a dentifrice composition. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01% to 10%, for example 0.05% to 5% or 0.1% to 2% by weight of the composition.

In a still further embodiment, the composition can optionally comprise at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of 200,000 to 7,000,000, for example 500,000 to 5,000,000 or 1,000,000 to 2,500,000. One or more PEGs are optionally present in a total amount of 0.1% to 10%, for example 0.2% to 5% or 0.25% to 2% by weight of the composition.

In a still further embodiment, the composition may include, but in certain embodiments does not include, at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly l-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. In certain embodiments, the thickening or gelling agents include a class of homopolymers of acrylic acid crosslinked with an alkyl ether of pentaerythritol or an alkyl ether of sucrose, or carbomers. Carbomers are commercially available from Lubrizol as the Carbopol® series. In certain embodiments, Carbopols include Carbopol 934, 940, 941, 956, 974P, and mixtures thereof. One or more thickening agents are optionally present in a total amount of 0.01% to 15%, for example 0.1% to 10% or 0.2% to 5% by weight of the composition.

In a still further embodiment, the composition optionally comprises at least one viscosity modifier, useful for example to inhibit settling or separation of ingredients or to promote redispersibility upon agitation of a liquid composition. Viscosity modifiers also may be present to increase the viscosity of the composition. Any orally acceptable viscosity modifier can be used, including without limitation mineral oil, petrolatum, clays and organomodified clays, silica and the like. One or more viscosity modifiers are optionally present in a total amount of 0.01% to 10%, for example 0.1% to 5% by weight of the composition. The viscosity modifier can be used to adjust the viscosity of the oral care composition to within the range of 1 to 100 mPas (cps).

In a still further embodiment, the composition optionally comprises at least one humectant, useful for example to solvate the high levels of hydrophobic flavorants, sensates, and active agents. Any orally acceptable humectant can be used, including without limitation polyhydric alcohols such as glycerin, propylene glycol, sorbitol, xylitol or low molecular weight PEGs. Most humectants also function as sweeteners. One or more humectants are optionally present in a total amount of 1% to 70%, for example 10% to 50%, 15% to 40%, or 20% to 30% by weight of the composition.

In a still further embodiment, the composition may comprise at least one colorant. Colorants may be employed to adjust the color, in the event the photosensitizing dye does not provide the appropriate aesthetically pleasing color. Colorants herein include pigments, dyes, lakes and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of 0.001% to 20%, for example 0.01% to 10% or 0.1% to 5% by weight of the composition.

In some embodiments, a solvent, such as ethanol, ethyl acetate, or acetone, may be added to improve the homogeneity of the solution and general solvation of hydrophobic agents, such as flavors, sensates and actives. In certain embodiments, the solvent is ethanol.

In accordance with another embodiment, there is provided a system comprising a toothbrush having at least one applicator element (e.g., a plurality of filaments) and a transfer mechanism for transfering an oral care composition from a reservoir positioned within the toothbrush to the surface of the at least one applicator element, and the oral care compositions described herein. The transfer mechanism for transfering may include wicking fibers, wicking foams, sponges, hydrogels, fluid passageways connecting a reservoir containing the composition to the filaments, vibration devices, pumps, and combinations thereof. The at least one applicator element may include, for example, a plurality of bristles, foam, fibers, and other cleaning devices.

In accordance with another embodiment, there is provided a method of administering an antibacterial agent to the oral cavity of a mammal comprising applying the oral care composition to the oral cavity. The method also contemplates applying the composition to the oral cavity by using a toothbrush with at least one applicator element and a transfer mechanism for transferring the oral care composition from a reservoir positioned within the toothbrush to the surface of the at least one applicator element, wherein the composition is transferred from the surface of the at least one applicator element to the oral cavity.

The toothbrush or applicator described herein is not critical to the embodiments, and any device capable of transferring a small amount of the oral composition from a reservoir stored in the device, to the tip of the applicator (e.g., bristles, foam pad, etc.) can be used. Some examples of suitable applicators are disclosed in U.S. Pat. Nos. 4,060,870; 5,407,287; 5,829,976; 6,205,611; 6,902,337; 6,932,603; and 6,932,604, and in U.S. Patent Application Publication Nos. 2001/0002228; 2003/0194678; 2005/0026103; 2007/0154863; and 2008/0176183. The device also may be any devices commercially available, including, for example, Squirtbrush® and Hyssop-Brush, both available through Case Dental & Medical Supply, Inc., www.cdmsupply.com. The applicator in certain embodiments includes at least one reservoir to contain the oral compositions described herein. The reservoir may be pre-filled with the composition, or may contain an inlet to permit filling and re-filling of the oral composition to the applicator.

In certain embodiments, the at least one applicator element comprises of bristles, foam, fiber, or other tooth cleaning devices, be positioned in certain embodiments at one end of the applicator, and be capable of transmitting fluid in the form of the oral compositions described herein. For example, the foam or fiber can be comprised of a material capable of wicking the composition from one end to the other. Bristles and other fibers also may be comprised of hollow filaments that permit the passage of minor amounts of fluids. Thus, when the oral composition is transmitted from the reservoir to the base of the bristles, foam, fiber, or other tooth cleaning device, that composition then can be transmitted further through the cleaning device to the surface of the bristles, foam, fiber, or other device and in contact with the oral cavity.

Any transfer mechanism capable of for transfering an oral care composition from a reservoir positioned within the toothbrush to the surface of the at least one applicator element can be used in the embodiments. Suitable transfer mechanisms include a capillary channel extending through at least a portion of the oral care implement connecting the reservoir to the at least one applicator element, and a vibration-producing device provided to vibrate the oral care implement and enhance transfer of the composition through capillary action. Another suitable transfer mechanism includes a capillary channel extending through at least a portion of the oral care implement connecting the reservoir to the at least one applicator element, and a pump that, when activated, is capable of pumping a pre-determined amount of fluid through the channel to the at least one applicator element. Another suitable transfer mechanism includes a wicking element positioned between the reservoir and the at least one applicator element capable of wicking the composition from the reservoir to the at least one applicator element. The wicking element may be capable of transferring the composition either by itself, or with the assistance of a pump, vibration device, gravity, pressure, or the like. Using the guidelines provided herein, and depending on the concentration of active ingredients in the composition, those skilled in the art will be capable of designing a suitable transfer mechanism for transferring the composition to deliver the requisite amount of active ingredient(s) to the oral cavity.

In one embodiment, the oral composition is applied by itself to the oral cavity. The inventors have discovered that only minor amounts of the oral care composition, on the order of 50 µl or less, can be delivered to the oral cavity, and still provide the same reduction in volatile sulfur compounds (VSC) as that obtained when using an antibacterial toothpaste, such as Colgate Total® toothpaste.

In another embodiment, the oral composition is applied to the oral cavity in connection with another dentifrice, such as a mouthwash, toothpaste, toothpowder, gum, and the like. In one embodiment, the oral composition is applied to the oral cavity during daily brushing using a toothpaste. The inventors have found that delivering about 45 µl of the oral composition to the oral tissue, in which the composition contained about 15% by weight of cetyl pyridinium chloride (CPC), resulted in about 7 mg of CPC delivered to the oral tissue. When an optional cooling agent is included in the oral composition and applied together with with conventional toothpaste, a sensory panel study produced results that showed a significantly higher cooling intensity for up to 20 minutes, when compared to brushing with just the toothpaste alone.

In various embodiments, the compositions are effective against a combination of oral bacteria, as shown for example, in artificial mouth antiplaque study. In various embodiments, superior VSC reduction and higher cooling intensities are realized when the oral compositions are delivered to oral tissue in the manner described herein.

The following are non-limiting examples.

SPECIFIC EMBODIMENTS

Prophetic Example A

The following is a prophetic example that is made by mixing of the ingredients similar to mixing described for Example 1 below.

| Material | Weight % |
|---|---|
| Antibacerial agent | 5 to 45 |
| Flavorant | 5 to 70 |
| Orally acceptable, liquid carrier | Q.S. |

Example 1

Oral care compositions having high concentrations of antibacterial actives and flavorants of certain embodiments are prepared by mixing the following ingredients (see Table 1). Several general procedures are followed regarding order of addition: flavors and oils are added to ethanol first; separately, in formulations with saccharin, phosphates, sodium citrate, citric acid, CPC or zinc, these are first added to the water; in some cases, CPC is first added to propylene glycol. Once fully dissolved, these ingredients and the remaining ingredients are combined and thoroughly mixed to produce a homogeneous solution. All examples described here are prepared at room temperature, although in some cases, it may be necessary to heat certain ingredients initially to fully dissolve them into the corresponding solvent base. It is generally advisable to cool all mixtures to room temperature before adding the ethanol/flavor, however, to minimize process losses. The examples are shown in Table 1 below:

TABLE 1

|  | I | II | III | IV | V | VI |
|---|---|---|---|---|---|---|
| Cetyl pyridinium chloride | 15 | 5 | 5 | 5 | 5 | — |
| Ethanol | 10 | 10 | 10 | 10 | 10 | 10 |
| Essential oils | — | 5.5 | 8.1 | 3 | 5.5 | — |
| Cooling flavor | 3 | 5.6 | 3 | 8.1 | — | 3 |
| Peppermint Flavor | 8.1 | — | — | — | — | 8.1 |
| Tea tree oil | — | — | — | — | — | 1 |
| Propylene Glycol | 7 | 7 | 7 | 7 | 7 | 7 |
| Glycerin | 15 | 15 | 15 | 15 | 15 | 15 |
| Citric acid | 0.06 | 0.06 | 0.06 | 0.06 | 0.06 | — |
| Sodium citrate | 0.51 | 0.51 | 0.51 | 0.51 | — | — |
| ZnCl | — | — | — | — | — | — |
| ZnCitrate | — | — | — | — | 0.3 | — |
| Poloxomer™ 407 nonionic surfactant | — | 5 | 5 | 5 | 5 | — |
| Tetrapotssium pyrophosphate | — | — | — | — | 1.35 | — |
| Tetrasodium pyrophosphate | — | — | — | — | 0.45 | — |
| Sodium lauryl sulfate | — | — | — | — | — | 5 |
| Sucralose | 1.5 | 0.5 | 0.5 | 0.5 | 0.5 | 0.5 |
| Water | balance | balance | balance | balance | balance | balance |

Laboratory tests were carried out to measure the delivery of the formula Example I in Table 1 onto a surface that mimics the oral tissue (in particular, porcine tongue). These studies indicate that an average of 45 µL of concentrated formulation was dispensed through a wicking system when in contact with soft tissue, when using a toothbrush such as those disclosed in U.S. Patent Application Publication Nos. 2007/00154863 and 2008/0176183. This volume was taken in consideration in order to develop a formula with 15% CPC, which was translated to 7 mg active delivered, comparable to mouthwash values (5 mg CPC/dose), even though a significantly higher volume of mouthwash is required to provide the same amount of active to the oral tissue.

A sensory panel study was carried out to study the potential of enhanced signal provided by the toothbrush wicking system mentioned above, when compared to a conventional toothbrush (e.g., Colgate® 360°® toothbrush, commercially available from Colgate Palmolive, New York, N.Y.). Panelists brushed the following surfaces for a total of 85 seconds using each product combination: upper molars and bicuspids and bottom chewing surfaces. The brush angle was kept at 45 degrees with the bristles pointing toward the gum/teeth line as much as possible during use. The tongue was also brushed 5 times back and forth using the tongue cleaner. Cooling intensity was evaluated immediately upon expectoration, and at the subsequent time intervals described below using a numerical scale 0-15. All samples were run in duplicate, and averages reported. There was a minimum of 1 hour between each evaluation The panel recorded the cooling intensity for: (a) application using Colgate® 360°® toothbrush with Colgate Cavity Protection, Great Regular Flavor toothpaste, both commercially available from Colgate Palmolive, New York, N.Y., (designated Comparison); and (b) application using Colgate Cavity Protection, Great Regular Flavor toothpaste on a wicking toothbrush such as those disclosed in U.S. Patent Application Publication Nos. 2007/00154863 and 2008/0176183 in which the oral composition contained within the reservoir had the formula of Example 1 (designated Invention). The results of the panel study are shown in Table II below.

TABLE II

Panel Study Cooling Intensity Results

| | | Cooling Intensity per time interval | | | | | | |
|---|---|---|---|---|---|---|---|---|
| Sample | Exp. | 1 min. | 3 min. | 5 min. | 10 min. | 15 min | 20 min | 25 min |
| Comparison | 5.0 | 5.9 | 5.9 | 4.0 | 3.0 | 3.0 | 3.0 | 3.0 |
| Invention | 6.4 | 9.8 | 9.8 | 7.7 | 5.1 | 4.0 | 3.3 | 3.0 |

The results of the panel study reveal that use of the oral composition of the invention provides significantly higher cooling intensity for up to 20 minutes after brushing, when compared to brushing with a conventional toothpaste alone.

Example 2

Additional oral care compositions were prepared in which the amounts of active ingredients were increased to even greater levels, but still within allowable safety limits. The viscosity of the formulations were measured within the range of 5-80 mPas (cps), when measured at 25° C. using a Brookfield Viscosimeter employing a cone spindle at 10 rpm (2 degrees, 40 mm). The additional formulations, one for flavor delivery and the others for antibacterial delivery or for both flavor and anti-bacterial delivery, are shown in Table III below.

TABLE III

| Ingredient Name | For Flavor Delivery Formulation A | For Anti-Bacterial Delivery Formulation B | Formulation C | Formulation D |
|---|---|---|---|---|
| Glycerin | 8 | 8 | 15 | 17.9 |
| 95% ethanol | 10 | 5 | 15 | 0 |
| PEG-40 Sorbitan Diisosterate | 40 | 40 | 0 | 0 |
| Flavor | 30 | 20 | 30 | 30 |
| Saccharin or Sucralose | 2.5 | 2.5 | 2.0 | 2.0 |
| Cetyl pyridinium chloride (CPC) | 0 | 10 | 15 | 15 |
| Poloxomer (Pluracare ®) | 0 | 0 | 0.1 | 0.1 |
| Proplene glycol | 0 | 0 | 17 | 20 |
| Purified water | 9.5 | 14.5 | 5.9 | 15 |
| Total Materials | 100 | 100 | 100 | 100 |

An in vitro assay was performed to assess the malodor reducing capacity of Formulation B in Table III above, in which the assay determined the percent reduction of volatile sulfur compounds (VSC). Aqueous solutions or dispersions of a comparative toothpaste (Colgate® Total®), a placebo base composition in water, a comparative composition containing 5% by weight CPC in water, and Formulation B were tested in an in vitro system consisting of whole human saliva, fluid thioglycolate medium, and DI water, and incubated for 3 hours at 37° C. in an airtight container. After incubation, the headspace VSC (volatile sulfur compounds) foiination was measured by an instrumental GC-flame photometric technique. Since mouth odor has been attributed to the presence of volatile sulfur compounds such as hydrogen sulfide, methyl mercaptan and dimethyl sulfide resulting from putrefactive processes occuring in the oral cavity, aforesaid in vitro test provide results comparable to in vivo sensory evaluations. The results, as set forth in Table IV, show excellent VSC inhibition for Formlation B of the invention, which was even better than Colgate® Total®, despite considerably lower amounts of composition tested (only 50 μl).

TABLE IV

| | Product | | | |
|---|---|---|---|---|
| | Colgate® Total® | Placebo Base | 5% CPC | Formulation B |
| % Inhibition VSC | 91 | 19 | 30 | 94 |

Formulation B, which contained 10% CPC is substantially equivalent to the standard dose of CPC received using the Plax Overnight mouthrinse. Table IV above reveals that a dose of only 50 μl of Formulation B, however, provided even better reduction in VSC than brushing with Colgate® Total®, an unexpectedly superior result.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

We claim:

1. An oral care composition comprising:
   (a) 5 to 45% by weight antibacterial agent selected from copper (II) compounds, zinc ion sources, phthalic acid and salts thereof, hexetidine, octenidine, sanguinarine, benzalkonium chloride, domiphen bromide, alkylpyridinium chlorides, iodine, sulfonamides, magnolia extract, grapeseed extract, menthol, geraniol, citral, eucalyptol, augmentin, amoxicillin, tetracycline, doxycycline, minocycline, metronidazole, neomycin, kanamycin and clindamycin;
   (b) 5 to 70% by weight flavorant; and
   (c) an orally acceptable liquid carrier,
   wherein the composition contains more than 5 mg of antibacterial agent per less than 50 μl of the composition, and wherein the composition has a viscosity of 1 to 100 mPas (cps), viscosity being measured at 25° C. using a Brookfield viscosimeter employing a cone spindle at 10 rpm (2 degrees, 40 mm).

2. The composition of claim 1, wherein the orally acceptable liquid carrier comprises water.

3. The composition of claim 2, wherein the orally acceptable, liquid carrier further comprises ethanol, optionally wherein a ratio of water to ethanol is 0.5:1 to 20:1, 0.75:1 to 10:1, or 1:1 to 7:1.

4. The composition of claim 1, wherein the composition contains about 7 mg of antibacterial agent per about 45 μl of the composition.

5. The composition of claim 1, wherein the viscosity of the composition is 5 to 30 mPas (cps).

6. The composition of claim 1, wherein the flavorant is present in an amount of 10% to 60% by weight.

7. The composition of claim 1 further comprising a sweetener, optionally present in an amount of 0.1% to 10% by weight.

8. The composition of claim 1, wherein at least a portion of the flavorant comprises a cooling agent.

9. A method of administering an antibacterial agent to the oral cavity of a mammal comprising applying the composition of claim 1 to the oral cavity.

10. The composition of claim 1, for use in a method of administering an antibacterial agent to the oral cavity of a mammal comprising applying the composition to the oral cavity.

\* \* \* \* \*